United States Patent [19]

Crawley

[11] 3,995,488
[45] Dec. 7, 1976

[54] DIELECTRIC CHANGE SENSING DEVICE

[75] Inventor: David Francis Charles Crawley, Keyworth, England

[73] Assignee: Fisons Limited, London, England

[22] Filed: June 10, 1975

[21] Appl. No.: 585,586

Related U.S. Application Data

[63] Continuation of Ser. No. 436,739, Jan. 25, 1974, abandoned, which is a continuation-in-part of Ser. No. 263,276, June 15, 1972, abandoned, which is a continuation-in-part of Ser. No. 49,353, June 24, 1970, abandoned.

[30] Foreign Application Priority Data

Nov. 16, 1971 United Kingdom ............ 53030/71

[52] U.S. Cl. .......................... 73/304 C; 324/61 R
[51] Int. Cl.² ........................................ G01F 23/00
[58] Field of Search ............... 73/304 C; 324/61 R, 324/61 P

[56] References Cited

UNITED STATES PATENTS 2,882,728   4/1959   Zito .................. 73/304 C

FOREIGN PATENTS OR APPLICATIONS 1,196,033   6/1970   United Kingdom ............ 324/61 R

*Primary Examiner*—Jerry W. Myracle
*Attorney, Agent, or Firm*—Wenderoth, Lind & Ponack

[57] ABSTRACT

A sensing head for use in the sensing of impedance changes includes a bridge circuit, a first diode and first resistor connected in series and a second diode and a second resistor connected in series. The first and second diodes are connected to a first junction which is adapted to be connected to a high frequency alternating voltage supply such that, in use, the diodes will pass electrical signals of opposite sign from the junction. The first and second resistors are connected to a second junction which is adapted to be connected in use to an output circuit. There are also provided a first capacitor, a plate of which is connected to a junction which is between the first diode and the first resistor, and a second capacitor, a plate of which is connected to a junction which is between the second diode and the second resistor. When in use, a change in the dielectric properties in a body adjacent to the first capacitor produces a change in the output signal across the output circuit. The bridge circuit is rigidly mounted within a conducting screen having an aperture adjacent to the first capacitor.

9 Claims, 3 Drawing Figures

DIELECTRIC CHANGE SENSING DEVICE

This is a continuation, of application Ser. No. 436,739, filed Jan. 25, 1974, now abandoned which is a continuation-in-part of application Ser. No. 263,276, filed June 15, 1972, now abandoned, which is a continuation-in-part of application Ser. No. 49,353, filed June 24, 1970, now abandoned.

BACKGROUND OF THE INVENTION

The present invention relates to a device for use in sensing dielectric changes in a solid, liquid or gas body.

A number of proposals have been made for converting changes in impedance or dielectric into electrical voltage, current or frequency changes. One design described by Marsh in Electronics, 20th Mar. 1967, uses the change in dielectric to control the frequency of an oscillator. The circuit however, is complex and suffers seriously from the effects of stray capacitance, this being particularly pronounced where the circuit is remote from the measuring capacitor, as it usually must be. Other oscillation devices also tend to be fairly insensitive and for similar reasons.

It has also been proposed to use radio frequency voltage sources in balancing circuits. These produce a direct current output, but again problems are encountered with stray capacitance and temperature drift, and these devices accordingly are of low sensitivity.

SUMMARY OF THE INVENTION

An object of the present invention is provided a relatively simple and compact device for use in the measurement of changes in dielectric and in which the aforesaid disadvantages are minimised.

In one aspect, the present invention provides a sensing head for use in the sensing of impedance changes, which sensing head comprises a bridge circuit having the following features:

a first diode and first resistor connected in series;

a second diode and a second resistor connected in series; the first and second diodes being connected to a first junction which is adapted to be connected to a high frequency alternating voltage supply such that, in use, the diodes will pass electrical signals of opposite sign from the junction; the first and second resistors being connected to a second junction which is adapted to be connected in use to an output circuit;

a first capacitor, a plate of which is connected to a junction which is between the first diode and the first resistor;

a second capacitor, a plate of which is connected to a junction which is between the second diode and the second resistor;

wherein, in use, a change in the dielectric properties in a body adjacent to the first capacitor produces a change in the output signal across the output circuit;

the bridge circuit being rigidly mounted within a conducting screen having an aperture adjacent to the first capacitor.

The first and second diodes may be thermionic diodes, semiconductor diodes, or any other diode or circuit equivalent thereto having suitable undirectional characteristics. Semiconductor diodes are preferred, and germanium diodes are particularly suitable because of their low shunt capacitance. The first and second diodes conveniently have the same characteristics, but this is not essential.

The resistance of the first and second resistors used will depend on the values of the other components in the circuit and its conditions of use. Thus, for example, resistors of the order of 200,000 to 300,000 ohms will generally be found to be suitable for an alternating voltage of 200 volts, peak to peak. The first and second resistors are suitably equal.

The construction of the first capacitor depends to some extent on the use for which the device is intended. For many applications, particularly where it is desired to mount the sensing head onto a tube, for example a thermometer, it has been found particularly useful if a metal spring clip, for example a 'Terry' clip, is used as a plate of the capacitor. Such a clip may be mounted, in use, onto a tube and the device may then be used to detect the movement of a meniscus in the tube. It is also suitable for a number of other applications.

It has been found that the sensing head will work using a first capacitor having only one plate. The reasons for this appear to be that the ambient atmosphere or adjacent objects are acting as an earthed second plate of the capacitor. In general, however, it is preferred that the first capacitor has two plates, since with only one plate, the sensitivity of the device may be reduced.

The second capacitor may be of a suitable fixed capacitance, but is preferably a variable capacitor, for example, a trimmer capacitor. A variable capacitor may be adjusted to give a desired first output signal. The capacitance of the second capacitor will depend on the outer components of the circuit, but a capacitor varying between 0.5 and 3 pico Farads has been found useful for many applications.

The electrical screen may be a housing of, for example, a metal such as aluminium, a metal-plated plastic such as chromiumplated ABS resin, a conducting plastic such as a carbon-filled plastic, or the like. The screen may be coated with a protective layer, for example of a polyethylene or polypropylene, to prevent corrosion. The screen preferable also acts as the second plate of the first capacitor.

As mentioned above, the screen must have an aperture adjacent to the first capacitor. This is to permit access to the first capacitor. The apertures may take the form of a simple hole in the screen, or slots through which a tube may be passed, or the like. Preferably, the screen is an open-ended box wherein the first capacitor is adjacent to the open end. The capacitor may project beyond the open end of the box or be contained behind an imaginary end wall.

The circuit is suitably rigidly mounted in the screen by means of an insulating polymer or resin, for example, an epoxy resin. It will be appreciated that the sensitive plate of the capacitor, particularly if in the form of a spring clip, should not be immersed in the polymer or resin. The resin or polymer prevents relative movement of the circuit components and prevents the ingress of moisture.

The sensing head may be manufactured so as to be both small and light in weight. Thus, the whole sensing head may be located at the measuring point, for example by mounting on a tube by means of a spring clip capacitor. With this arrangement, there need be no long electrical leads running from one part off the sensing circuit to another and the stray capacitances are thereby reduced so as to be negligible. In addition, the rigid mounting in the screen prevents stray capacitance arising from people passing or from relative movement between the circuit components. The output signal from the head takes the form of voltage changes which are easily measured and, if screened cable is used for connection to the output circuit, are not subject to random capacitative influences as, for example, are those devices in which the output signal is a change in frequency. Thus the device is highly sensitive, with the additional merit of being relatively simple, robust and compact.

In use, the device is connected to a high frequency alternating voltage supply. The voltage used is not critical and 200–250 volts, peak to peak has been found to be suitable for most purposes. The sensitity of the device increases with the alternating frequency, but at very high frequencies, the device may suffer from the effects of shunt capacitance. The frequency chosen is therefore to some extent a compromise. Frequencies of 150 to 250 Hz have been found particularly useful. The output from a sensing head connected in this way is direct current, and may be subject to temperature drift, thereby reducing the sensitivity of the device. It has been found, however, that by using a modulated high frequency voltage, and a direct current blocking capacitor in the output circuit, a pulse signal can be obtained which is both simple to measure and easy to stabilise. The modulation may be of any convenient low frequency, such as 50 cycles per second — this being the mains frequency in the United Kingdom.

The output signal, preferably amplified, may be fed to an alarm, control, counting, recording or other desired detecting mechanism. Thus the output signals from the device may be used to control the level of liquid in a tube, to count the number of crystals or grains falling past the device, or the number of objects fed past the device, or the device may be used to detect changes in the dielectric properties of a gas or other body, and, for example, record or count these changes.

BRIEF DESCRIPTION OF THE DRAWINGS

The device according to the present invention will now be illustrated by the accompanying drawings in which.

DETAILED DESCRIPTION OF THE INVENTION

Figure 1:
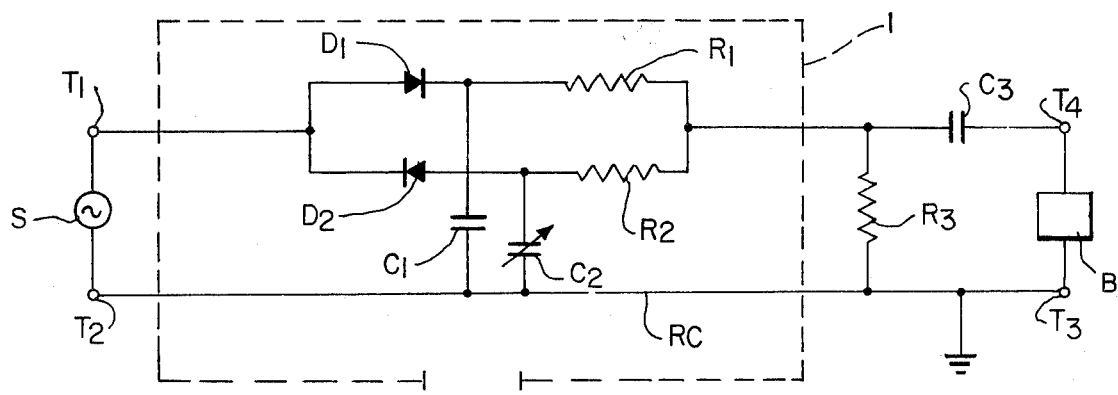
FIG. 1 is a circuit diagram of the sensing head, and also showing a circuit of an output circuit.

Referring now to FIG. 1, the circuit housed in the sensing head is shown enclosed by screen 1 shown by a broken line. The circuit consists of diodes D1 and D2, and resistors R1 and R2, connected into a bridge circuit with a sensing capacitor C1 and a variable balancing capacitor C2. The circuit is connected to a high frequency alternating voltage S. The output circuit includes a load resister R3 and a direct current blocking capacitor C3. An amplification circuit for the output circuit is shown diagramatically at B.

Figure 2:
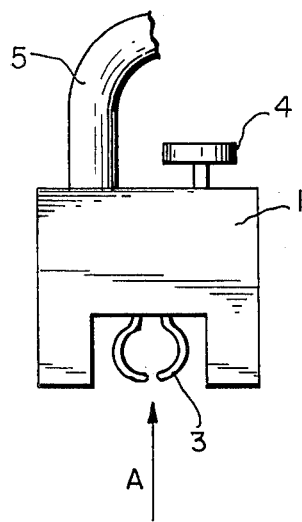
FIG. 2 is a plan view of a sensing head suitable for use with the circuit of FIG. 1.

Referring now also to FIG. 2, the sensing head comprises an earthed metallic screen 1 housing the circuit components enclosed in the dotted line shown in FIG. 1. The circuit components, apart from the capacitor C1, are embedded in solid insulating epoxy resin 2. A Terry clip 3, mounted on the resin 2, forms the sensitive plate of the first capacitor C1 of FIG. 1, and the screen 1 forms the other plate. A rotatable control knob 4 projects from the back of the screen 1 for controlling the setting of the variable capacitor C2 of FIG. 1. Screened cable 5 connects the circuitry enclosed in the screen 1 to the other circuit components, which are conveniently housed in a separate unit (not shown) which suitably also contains a pulse amplified circuit and a circuit for producing a modulated high frequency alternating voltage.

Figure 3:
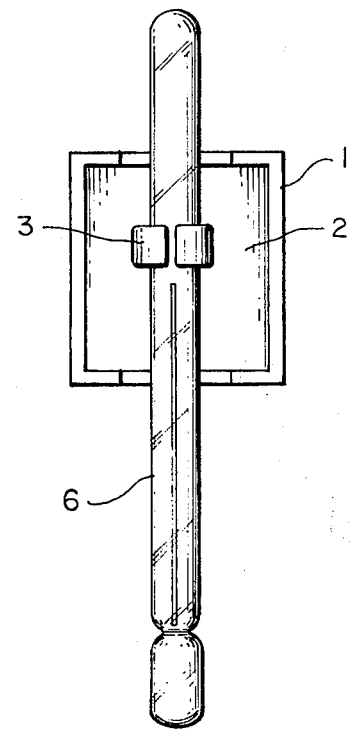
FIG. 3 is a side view of the sensing head of FIG. 2, viewed in the direction of the Arrow A, mounted on a thermometer ready for use.

To use the device shown in FIGS. 1 to 3 on a thermometer 6 to detect a temperature rise above a maximum setting, the device is connected to the amplifier B and modulated high frequency alternating voltage supply S. The sensing head is mounted on the thermometer 6, by means of the clip 3, such that the clip surrounds the level of the liquid in the thermometer. The control knob 4 is rotated to produce the desired output signal (preferably to substantially zero), and the sensing head is moved such that the clip surrounds the required maximum temperature setting and thereby changes the balance of the circuit. If the thermometer temperature rises above the required maximum, the liquid in the thermometer restores the balance of the circuit, thereby changing or producing an output signal, which is amplified by the amplifier.

The amplified signal may be fed to a visual or aural alarm, and/or may be fed to a control device which controls, for example, a heating system.

In a similar way, the device may be used for detecting changes in liquid levels in other tubes, such as manometers.

The described device may also be used, with or without modification, to detect liquid levels in larger containers. In this case, the open end of the sensing head is pressed against the wall of the container.

The described device may also be used to count moving objects. The sensing head is placed with its open end adjacent to the path of the moving objects. An object passing the sensing head will change the balance of the circuit and produce an output signal. This may be amplified and fed to a count mechanism or other recorder as desired.

There are a number of modifications which may be made to the above device to vary its use, sensitivity or the like. Thus, the resistor R1 may be replaced by a resistor of lower value than R2 and a third resistor which is variable and used to achieve a fine balance of the bridge. Further, if desired, other circuit components, such as resistor R3 and/or capacitor C3 may be housed in the screen. Alternative capacitor plates may be used in place in the spring clip, for example a flat plate or a U-shaped plate, according to the intended use of the device.

I claim:

1. A sensing device for use in the sensing of impedance changes, which sensing device comprises a sensing head and an output circuit connected thereto, wherein the sensing head comprises a bridge circuit and a conducting screen in the form of an open-ended box within which the bridge circuit is rigidly mounted, said bridge circuit comprising:
    a. a first diode and first resistor connected in series;
    b. a second diode and a second resistor connected in series; the first and second diodes being connected to a first junction which is adapted to be connected to a modulated high frequency alternating voltage supply such that, in use, the diodes will pass electrical signals of opposite sign from the junction; the first and second resistors being connected to a second junction;

c. a first capacitor, the plates of which are connected respectively to earth and to a junction which is between the first diode and the first resistor; and d. a second capacitor, the plates of which are connected respectively to earth and to a junction which is between the second diode and the second resistor; the conducting screen having an aperture therein adjacent to the first capacitor; and said output circuit comprising:

i. a direct current blocking capacitor, one plate of which is connected to said second junction, and the other plate of which provides the output from the device; and ii. a load resistor connected between said second junction and earth; wherein, in use, a change in the dielectric properties in a body adjacent to the first capacitor produces a change in the pulsed output signal from said output provided by said direct current blocking capacitor.

2. A sensing device as claimed in claim 1, wherein said first capacitor is a single metal spring clip.

3. A sensing device as claimed in claim 1, wherein said open-ended box is a housing of metal, metal-plated plastic or conducting plastic.

4. A sensing device as claimed in claim 1, wherein said screen comprises one of the plates of said first capacitor.

5. A sensing device as claimed in claim 1, wherein said bridge circuit is rigidly mounted within said screen by means of an insulating polymer or resin.

6. In a device for the sensing of changes in impedance by means of a balancing bridge circuit of the type including a sensing capacitor and a balancing capacitor, the improvement wherein the balancing bridge circuit is rigidly mounted within a conductive screen having an aperture adjacent to the sensing capacitor.

7. A device as claimed in claim 6, wherein one plate of said sensing capacitor is a spring clip and the other plate is formed by said screen.

8. A device as claimed in claim 6, wherein said screen is an open-ended box.

9. A device as claimed in claim 6, wherein said bridge circuit is rigidly mounted within said screen by means of an insulating polymer or resin.

* * * * *